US00PP25581P2

(12) United States Plant Patent
Catt

(10) Patent No.: US PP25,581 P2
(45) Date of Patent: May 26, 2015

(54) ***PEROVSKIA* PLANT NAMED 'LISSVERY'**

(50) Latin Name: *Perovskia atriplicifolia*
Varietal Denomination: Lissvery

(71) Applicant: Peter Catt, Liss (GB)

(72) Inventor: Peter Catt, Liss (GB)

( * ) Notice: Subject to any disclaimer, the term of this patent is extended or adjusted under 35 U.S.C. 154(b) by 28 days.

(21) Appl. No.: 13/986,364

(22) Filed: Apr. 23, 2013

(51) Int. Cl.
*A01H 5/02* (2006.01)

(52) U.S. Cl.
USPC ..... Plt./263.1

(58) Field of Classification Search
CPC ..... A01H 5/00
USPC ..... Plt./263.1, 226
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of *Perovskia* plant named 'LISSVERY', characterized by its plant habit that is compact and bushy during early growth and becoming erect at flowering, its wide lanceolate shaped leaves with margins that have shallow dissections, its foliage that is light sage green when young and matures to a silvery-pale green, its stiff flowering stems that are held upright with short internodes, and its violet blue flowers with distinct calyces that are showy after petal drop.

2 Drawing Sheets

Botanical classification: *Perovskia atriplicifolia*.
Variety denomination: 'LISSVERY'.

CROSS REFERENCE TO A RELATED APPLICATION

This application is co-pending with a U.S. Plant Patent Application filed for a plant derived from the same breeding program that is entitled *Perovskia* Plant Named 'LISSLITT' (U.S. Plant Pat. No. 20,845).

BACKGROUND OF THE INVENTION

The present invention relates to a new and distinct cultivar of *Perovskia* plant, botanically known as *Perovskia atriplicifolia* 'LISSVERY' and will be referred to hereinafter by its cultivar name, 'LISSVERY'. The new cultivar of *Perovskia* is a hardy herbaceous perennial grown for garden use.

'LISSVERY' resulted from an ongoing breeding project by the Inventor at his nursery in Liss, Hampshire, United Kingdom. The Inventor collected seeds in 2000 from self-pollinated plants of *Perovskia atriplicifolia* 'Blue Spire' (not patented), the collected seeds were sown in 2001 and the new cultivar was selected as a single unique plant from the resulting seedlings in 2002. The Inventor conducted a 3-year garden trial with known cultivars of *Perovskia* in 2008, 2009, and 2010.

Asexual propagation of the new cultivar was first accomplished by the Inventor by stem cuttings in 2003 in Liss, Hampshire, United Kingdom. Asexual propagation by stem cuttings has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'LISSVERY' as a unique cultivar of *Perovskia*.

1. 'LISSVERY' exhibits a plant habit that is compact and bushy during early growth and becoming erect at flowering.
2. 'LISSVERY' exhibits wide lanceolate shaped leaves with margins that have shallow dissections.
3. 'LISSVERY' exhibits foliage that is light sage green when young and matures to a silvery-pale green.
4. 'LISSVERY' exhibits very stiff flowering stems that are held upright with short internodes.
5. 'LISSVERY' exhibits violet blue flowers with distinct calyces that are showy after petal drop.

The parent plant, 'Blue Spire', differs from 'LISSVERY' being taller in height, in having foliage with longer internodes, and in having a more open plant habit. 'LISSVERY' can be most closely compared to the cultivars 'Little Spire' (U.S. Plant Pat. No. 11,643) and 'LISSLITT'. 'Little Spire' differs from 'LISSVERY' in having much smaller and narrower leaves. 'LISSLITT' differs from 'LISSVERY' in being shorter in height with less stiff stems, in having foliage with longer internodes, narrower more fern-like leaves that are less silver in color, and in having flowering spikes that appear earlier in the season with flowers that have larger calyces.

BRIEF DESCRIPTION OF THE DRAWINGS

The accompanying colored photographs illustrate the overall appearance and distinct characteristics of the new *Perovskia*. The photographs were taken of plants grown outdoors in a garden in Liss, Hampshire, United Kingdom.

The photograph in FIG. 1 provides a side view of two plants of 'LISSVERY' about one year in age and illustrates its plant habit.

Figure 1:
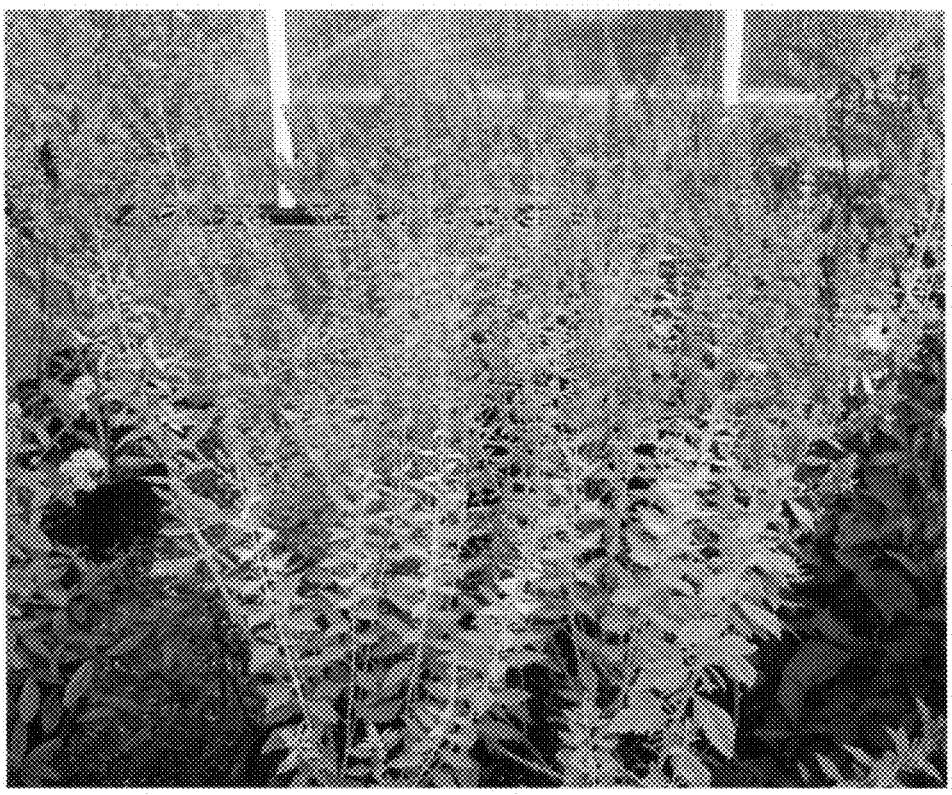
Figure 2:
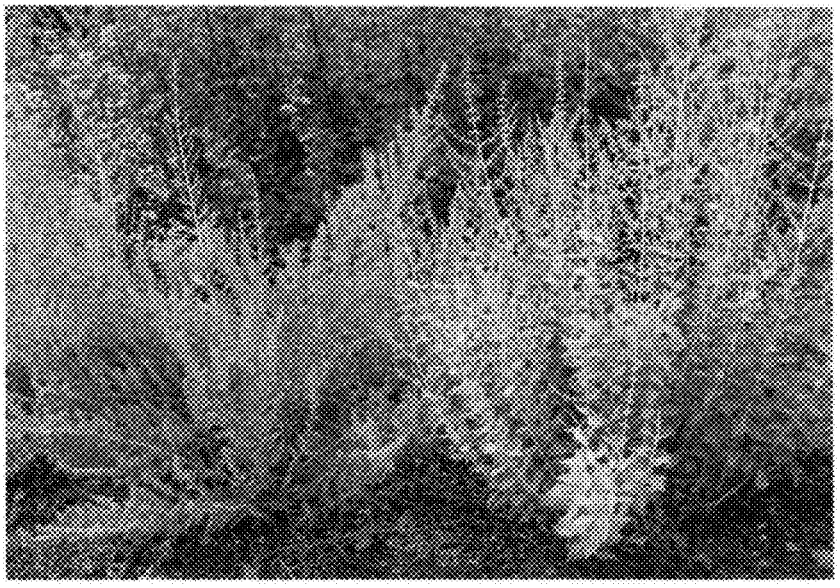
Figure 3:
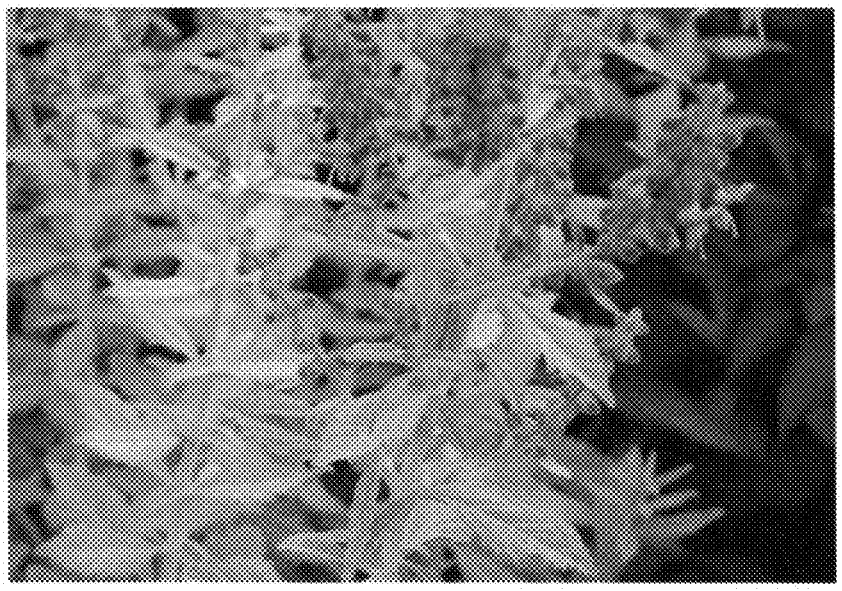

The photographs in FIG. 2 and FIG. 3 were taken of plants about two years in age. The photograph in FIG. 2 provides a comparison of 'LISSLITT' on the left and 'LISSVERY' on the right. The photograph in FIG. 3 provides a close up view of the foliage and flowers of 'LISSVERY'.

The colors in the photographs may differ slightly from the color values cited in the detailed botanical description, which accurately describe the colors of the new *Perovskia*.

DETAILED BOTANICAL DESCRIPTION

The following is a detailed description of two year-old plants of the new cultivar as grown outdoors in three-liter containers in Liss, Hampshire, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late July to September in southern United Kingdom with calyces remaining attractive for another several weeks.

*Plant type.*—Deciduous semi-woody sub-shrub.

*Plant habit.*—Compact and bushy during early growth and becoming erect at flowering.

*Height and width.*—Reaches about 60 cm in height and 30 cm in width.

*Hardiness.*—At least in U.S.D.A. Zones 5 to 9.

*Diseases and pests.*—No susceptibility or resistance to diseases or pests has been observed.

*Root description.*—Fibrous.

*Root initiation.*—Occurs in 14 to 21 days at an average temperature of 20° C.

*Root development.*—About 20 weeks to fully develop in a 1-liter container.

*Propagation.*—Stem cuttings.

*Growth rate.*—Moderately vigorous.

Branch description:

*Branch shape.*—Square.

*Branch color.*—190D.

*Branch size.*—Average of 4 mm in diameter and 50 cm in length.

*Branch surface.*—Pubescent, densely felted with stellate and simple hairs.

*Branching habit.*—Dense basal branching, an average of 60 basal branches on a plant two years in age in the garden.

Foliage description:

*Leaf division.*—Simple.

*Leaf arrangement.*—Opposite.

*Leaf shape.*—Elliptic to broadly lanceolate.

*Leaf size.*—Average of 4.5 cm in length and 1.4 cm in width.

*Leaf base.*—Cuneate.

*Leaf apex.*—Acute.

*Leaf margin.*—Irregularly toothed.

*Leaf venation.*—Pinnate, young leaves upper and lower surface; 190D, older leaves upper and lower surface; 191C.

*Leaf attachment.*—Petiolate to almost sessile.

*Leaf surface.*—Upper and lower surface; pubescent with scattered stellate and simple hairs.

*Leaf number.*—An average of 27 leaves per branch.

*Leaf internode length.*—Average of 1.5 cm.

*Leaf color.*—Young upper surface; 188C, young leaves lower surface; 190C, mature leaves upper surface; 191A, mature lower surface; 191B.

*Petiole.*—Average of 2 mm in length and 1 mm in diameter, young leaves are 190D in color, older leaves are 191C in color, surface is pubescent with scattered stellate and simple hairs.

*Foliage fragrance.*—Aromatic.

Inflorescence description:

*Inflorescence type.*—Terminal branched panicle of verticillicasters of bilabiate flowers.

*Lastingness of inflorescence.*—Individual flowers about 6 days with calyx persisiting for about 3 weeks longer.

*Inflorescence size and arrangement.*—29 to 35 cm in length, flowers in interrupted whorls with up to 12 flowers in each whorl, average of 12 mm between each whorl, 4 to 8 lateral branches are 8 to 12 cm in length and held at 45°.

*Flower type.*—Bilabiate.

*Flower number.*—Over 100 per inflorescence.

*Flower fragrance.*—Aromatic.

*Flower buds.*—Ovoid to globose in shape, about 4 mm in length and 3 mm in diameter, N88B in color, 4 to 5 weeks from visible bud to fully open flower.

*Flower size.*—About 1 cm in length and 8 mm in diameter.

*Peduncles.*—No obvious peduncle below lowest flowers, length of inflorescence is 35 cm, and an average of 2 mm in width, between 190C and N189D in color, surface is densely felted with stellate and simple hairs, an internode length of about 15 mm.

*Pedicels.*—About 1 mm in length and <1 mm in width, between 190C and N189D in color, surface is pubescent.

*Calyx.*—Tubular, 4 mm in diameter and 6 mm in height, 2-lipped; upper lip 3 toothed, lower lip is 2 toothed, persistant after petals have fallen for about 3 weeks.

*Sepals.*—5, fused at base with apex free; triangular in shape and <1 mm in length and width, margins fused into tube with apices entire, covered in shaggy tangled eglandular hairs 0.5 mm in length, color; N87B, shaded side is 191A, exposed side is N92C.

*Petals.*—5 lobes arranged in 2 lips fused into tube at base, tube; about 6 mm in length and 1 mm at base widening to 2 mm at the apex, color 94C, all lobes; entire margins, smooth surface, upper lip; 4-lobed, held upright to 90° to tube to slightly bent backwards, about 5 mm in length and 8 mm in width, between 94A and 93C in color, lower lip; 1 lobed, ovate in shape, about 5 mm in length and 4 mm in width and 94C in color.

Reproductive organs:

*Gynoecium.*—1 Pistil, style is about 7 mm in length, <1 mm in width and N155C in color and very slightly flushed with 94D towards apex, stigma is bi-fid, <1 mm in width and debth and N155C in color, ovary is superior, 4-lobed, <0.5 mm in diameter and to small to be measured with R.H.S. Colour Chart.

*Androecium.*—2 stamens, adnate to corolla and exserted, filaments are about 4 mm in length, <1 mm in width and N155C in color, anthers are about 1 mm in length and 94A in color, pollen is moderate in quantity and 11D in color.

*Seed.*—Very small, ovoid in shape, <0.5 mm in length and 0.5 mm in width, about 200A in color.

It is claimed:

1. A new and distinct variety of *Perovskia* plant named 'LISSVERY' as described and illustrated herein.

* * * * *